US012751791B2

(12) United States Patent
Rosati et al.

(10) Patent No.: US 12,751,791 B2
(45) Date of Patent: Oct. 6, 2026

(54) MIXED REALITY SURGICAL HELMET

(71) Applicant: Zimmer, Inc., Warsaw, IN (US)

(72) Inventors: Giorgio Rosati, Rome (IT); Carlo Gaino, Borgo Veneto (IT); Giorgio Gaino, Borgo Veneto (IT); Lorenzo Secco, Treviso (IT)

(73) Assignee: Zimmer, Inc., Warsaw, IN (US)

( * ) Notice: Subject to any disclaimer, the term of this patent is extended or adjusted under 35 U.S.C. 154(b) by 184 days.

(21) Appl. No.: 18/591,638

(22) Filed: Feb. 29, 2024

(65) Prior Publication Data

US 2024/0299126 A1 Sep. 12, 2024

Related U.S. Application Data

(60) Provisional application No. 63/450,414, filed on Mar. 7, 2023.

(51) Int. Cl.
*A61B 90/00* (2016.01)
*G02B 27/01* (2006.01)

(52) U.S. Cl.
CPC .......... *A61B 90/37* (2016.02); *G02B 27/0176* (2013.01); *A61B 2090/365* (2016.02)

(58) Field of Classification Search
CPC .............. A61B 90/37; A61B 2090/365; G02B 27/0176; G02B 27/2214; H04N 13/0404; H04N 13/0409; H04N 13/0497; H04N 13/0055
USPC .......................................................... 359/462
See application file for complete search history.

(56) References Cited

U.S. PATENT DOCUMENTS

| | | | |
|---|---|---|---|
| 6,481,019 B2 | 11/2002 | Diaz et al. | |
| 6,622,311 B2 | 9/2003 | Diaz et al. | |
| 7,752,682 B2 | 7/2010 | Vanderwoude et al. | |
| 8,282,234 B2 | 10/2012 | Vanderwoude et al. | |
| 11,857,378 B1 * | 1/2024 | Bojarski | G06F 3/013 |
| 2007/0050898 A1 | 3/2007 | Larson et al. | |
| 2018/0049622 A1 | 2/2018 | Ryan et al. | |
| 2018/0084848 A1 | 3/2018 | Pavalarajan et al. | |
| 2019/0212772 A1 | 7/2019 | Chen et al. | |
| 2019/0231005 A1 | 8/2019 | Jefferis et al. | |
| 2021/0298835 A1 | 9/2021 | Wang | |
| 2021/0307442 A1 * | 10/2021 | Yamada | G09G 5/10 |
| 2022/0015854 A1 | 1/2022 | Behera et al. | |

(Continued)

FOREIGN PATENT DOCUMENTS

| | | |
|---|---|---|
| JP | 2023113136 A | 8/2023 |
| WO | 2020070662 | 4/2020 |

OTHER PUBLICATIONS

"European Application Serial No. 23154643.3, Extended European Search Report mailed Jun. 19, 2023", 8 pgs.

(Continued)

*Primary Examiner* — Henry Duong
(74) *Attorney, Agent, or Firm* — Schwegman Lundberg & Woessner, P.A.

(57) ABSTRACT

A surgical helmet assembly can be securable to a mixed reality device. The assembly can include an inner frame securable to the mixed reality device and a visor. The visor can be releasably securable to the inner frame and the visor can be configured to optically expose the mixed reality device to a surgical field. The surgical hood can be connected to the visor and can be configured to cover at least a portion of a head of a user.

19 Claims, 8 Drawing Sheets

(56) References Cited

U.S. PATENT DOCUMENTS

| | | | |
|---|---|---|---|
| 2023/0240405 | A1 | 8/2023 | Spooner et al. |
| 2025/0017687 | A1 | 1/2025 | Chav et al. |

OTHER PUBLICATIONS

"European Application Serial No. 23154643.3, Response Filed Dec. 7, 2023 to Extended European Search Report mailed Jun. 19, 2023", 9 pgs.
"Canadian Application Serial No. 3,187,694, Examiners Rule 862 Report mailed May 30, 2024", 8 pgs.
"U.S. Appl. No. 18/100,252, Non Final Office Action mailed May 8, 2025", 14 pgs.
"U.S. Appl. No. 18/100,252, Response filed Aug. 8, 2025 to Non Final Office Action mailed May 8, 2025", 10 pgs.
"U.S. Appl. No. 18/100,252, Final Office Action mailed Sep. 25, 2025", 18 pgs.
"U.S. Appl. No. 18/100,252, Examiner Interview Summary mailed Dec. 9, 2025", 2 pgs.

* cited by examiner

MIXED REALITY SURGICAL HELMET

CLAIM OF PRIORITY

This application claims the benefit of U.S. Provisional Patent Application Ser. No. 63/450,414, filed on Mar. 7, 2023, the benefit of priority of which is claimed hereby, and which is incorporated by reference herein in its entirety.

BACKGROUND

Surgical advancements have allowed surgeons to use preoperative planning, display devices within a surgical field, optical imaging, and guides to improve surgical outcomes and customize surgery for a patient. While these advances have allowed for quicker and more successful surgeries, they rely on physical objects, which have costs and time requirements for manufacturing and configuration. Physical objects and devices can also obstruct portions of a surgical field.

Computer-assisted surgery is a growing field that encompasses a wide range of devices, uses, procedures, and computing techniques, such as surgical navigation, preoperative planning, and various robotic techniques. In computer-assisted surgery procedures, a robotic system can be used in some surgical procedures, such as orthopedic procedures, to aid a surgeon in completing the procedures more accurately, more quickly, or with less fatigue.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Mixed reality devices can be used during surgeries to help improve surgical performance or to help surgeons or physicians interact with surgical robots (or other devices) during the surgery using surgical instruments and a mixed reality interface. While mixed reality devices can help to increase surgical efficiency or accuracy, mixed reality devices can be relatively expensive and therefore not disposable and can also be relatively difficult to sterilize between procedures.

This disclosure helps to address these issues by providing a surgical helmet assembly to provide protection or covering over the mixed reality device to help minimize exposure of the mixed reality device to the surgical environment. The assembly can interface with a mixed reality device where the assembly can be releasably securable to disposable or cleanable components (such as a visor and a drape or hood) while positioning the lenses to allow the mixed reality device to operate properly through the visor. The assembly can include an inner frame securable to the mixed reality device and an outer frame secured, or securable, to the inner frame where the outer frame can include (or be connected to, possibly releasably) a visor and hood. The visor and hood can be released from the mixed reality device and inner frame for cleaning or disposal of the outer frame while the inner frame and mixed reality device can be hand-sterilized, allowing for reuse of the mixed reality device and the inner frame without high temperature sterilization.

For example, a surgical helmet assembly can be securable to a mixed reality device. The assembly can include an inner frame securable to the mixed reality device and a visor. The visor can be releasably securable to the inner frame and the visor can be configured to optically expose the mixed reality device to a surgical field. The surgical hood can be connected to the visor and can be configured to cover at least a portion of a head of a user.

The above discussion is intended to provide an overview of subject matter of the present patent application. It is not intended to provide an exclusive or exhaustive explanation of the invention. The description below is included to provide further information about the present patent application.

Figure 1:
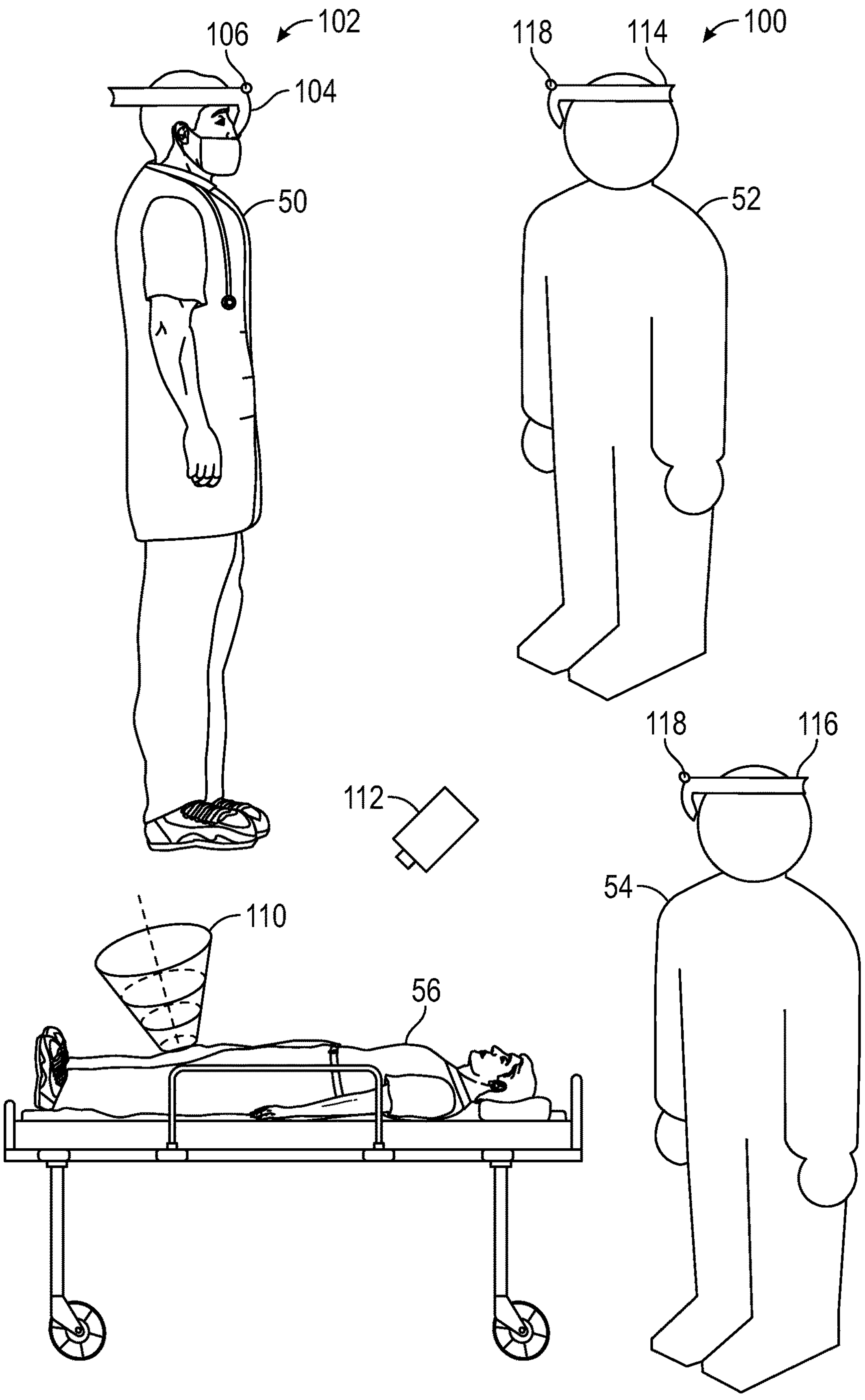
FIG. 1 illustrates surgical field in accordance with some embodiments.

FIG. 1 illustrates a surgical field 100 in accordance with some embodiments. The surgical field 100 illustrated in FIG. 1 can include a surgeon 50, a patient 56, and can include a camera 112. The surgeon 50 can wear a surgical helmet assembly 102 (examples of which are discussed below in further detail) that can include augmented reality (AR) or mixed reality (MR) device 104 which can be used to display a virtual object 110 to the surgeon 50. The virtual object 110 may not be visible to others within the surgical field 100 (e.g., surgical assistant 52 or nurse 54), though they may wear AR or MR devices 114 and 116 respectively (which can include cameras 118 and 120, respectively). Even if another person is viewing the surgical field 100 with an AR or MR device, the person may not be able to see the virtual object 110 or may be able to see the virtual object 110 in a shared augmented reality with the surgeon 50, or may be able to see a modified version of the virtual object 110 (e.g., according to customizations unique to the surgeon 50 or the person) or may see different virtual objects entirely. Augmented reality is a technology for displaying virtual or "augmented" objects or visual effects overlaid on a real environment. Mixed reality is a similar technology where visual effects are anchored or located relative to real objects in an environment. The disclosure herein can apply to either technology.

The real environment can include a room or specific area (e.g., the surgical field 100), or can be more general to include the world at large. The virtual aspects overlaid on the real environment can be represented as anchored or in a set position relative to one or more aspects of the real environment. For example, the virtual object 110 can be configured to appear to be resting on a table. An AR or MR system can present virtual aspects that are fixed to a real object without regard to a perspective of a viewer or viewers of the system (e.g., the surgeon 50). For example, the virtual object 110 can exist in a room, visible to a viewer of the system within the room and not visible to a viewer of the system outside the room. The virtual object 110 in the room can be displayed to the viewer outside the room when the viewer enters the room. In this example, the room can act as a real object that the virtual object 110 can be fixed to in the system.

The MR device 104 can include one or more screens, such as a single screen or two screens (e.g., one per eye of a user). The screens can allow light to pass through the screens such that aspects of the real environment are visible to the surgeon 50 while displaying the virtual object 110. The virtual object 110 can be made visible to the surgeon 50 by projecting light. The virtual object 110 can appear to have a degree of transparency or can be opaque (i.e., blocking aspects of the real environment).

An MR system can be viewable to one or more viewers, and can include differences among views available for the one or more viewers while retaining some aspects as universal among the views. For example, a heads-up display can change between two views while virtual objects can be fixed to a real object or area in both views. Aspects such as a color of an object, lighting, or other changes can be made among the views without changing a fixed position of at least one virtual object.

A user can see the virtual object 110 presented in an MR system as opaque or as including some level of transparency. In an example, the user can interact with the virtual object 110, such as by moving the virtual object 110 from a first position to a second position. For example, the user can move an object with his or her hand. This can be done in the MR system virtually by determining that the hand has moved into a position coincident or adjacent to the object (e.g., using one or more cameras, which can be mounted on an MR device, such as MR device camera 106 or separate, and which can be static or can be controlled to move), and causing the object to move in response. Virtual aspects can include virtual representations of real world objects or can include visual effects, such as lighting effects, etc. The MR system can include rules to govern the behavior of virtual objects, such as subjecting a virtual object to gravity or friction, or can include other predefined rules that defy real world physical constraints (e.g., floating objects, perpetual motion, etc.). An MR device 104 can include a camera 106 (not to be confused with the camera 112, separate from the MR device 104). The MR device camera 106 or the camera 112 can include an infrared camera, an infrared filter, a visible light filter, a plurality of cameras, a depth camera, etc. The MR device 104 can project virtual items over a representation of a real environment, which can be viewed by a user.

Eye tracking can be used with a MR system to determine which instrument a surgeon wants next by tracking the surgeon's eye to the instrument. In an example, a nurse or surgical assistant can then retrieve the determined instrument. The determined instrument can be presented in MR to the nurse or surgical assistant. In another example, the surgeon can speak the instrument (e.g., using a pre-selected code word, using speech processing and word recognition, via saying a number, or the like). The voice command can be combined with eye tracking, in still another example, to find an instrument.

The MR device 104 can be used in the surgical field 100 during a surgical procedure, for example performed by the surgeon 50 on the patient 56. The MR device 104 can project or display virtual objects, such as the virtual object 110 during the surgical procedure to augment the surgeon's vision. The surgeon 50 can control the virtual object 110 using the MR device 104, a remote controller for the MR device 104, or by interacting with the virtual object 110 (e.g., using a hand to "interact" with the virtual object 110 or a gesture recognized by the camera 106 of the MR device 104). The virtual object 108 can augment a surgical tool. For example, the virtual object 110 can appear (to the surgeon 50 viewing the virtual object 110 through the MR device 104) as a representation of a landmark previously placed on a patient bone. In another example, the virtual object 110 can be used to represent a planned location of a landmark (e.g., using a pre-operative image and a captured image of the bone in the real space). In certain examples, the virtual object 110 can react to movements of other virtual or real-world objects in the surgical field. For example, the virtual object 110 can be altered by a to move a landmark (e.g., a placed landmark). In other examples, the virtual object 110 can be a virtual representation of a remote surgical field (e.g., an entire OR, a camera field of view of a room, a close-up view of a surgical theater, etc.). In this example, the virtual object 110 can include a plurality of virtual objects.

Figure 2A:
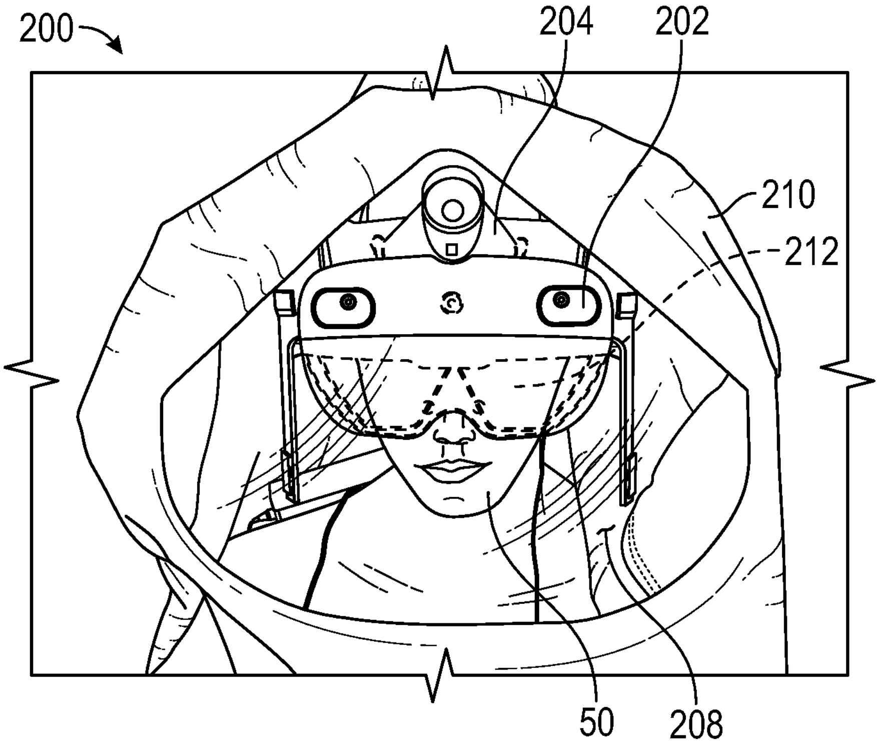
FIG. 2A illustrates a perspective view of a surgical helmet assembly.

FIG. 2A illustrates a perspective view of a surgical helmet assembly 200, which can be similar to the surgical helmet 102 discussed above. The surgical helmet assembly 200 is discussed in greater detail below. FIG. 2 also shows a user 50 or surgeon.

The surgical helmet assembly 200 can include an MR device 202, which can be similar to any of the AR or MR devices discussed above. The MR device 202 can be securable to a head of the surgeon 50 such as for performing a robotic-assisted (or other) procedure. The surgical helmet assembly 200 can also include an inner frame 204 securable to the MR device 202 and the surgical helmet assembly 200 can include an outer frame 206. The outer frame 206 can include a visor 208 and a hood 210, where the visor 208 can be connected to the hood 210.

The visor 208 can be a transparent or translucent shield configured to provide visibility for the surgeon 50 while limiting transfer of matter between the surgeon 50 and the surgical environment. The hood 210 can be a drape or covering secured to a perimeter of the visor 208 or the outer frame 206. The hood 210 can be configured to cover at least a portion of a head of the surgeon 50 when donned by the surgeon 50. The outer frame 206 or visor 208 can be releasably securable to the inner frame 204 to enclose at least a portion of the head and neck of the surgeon 50 in the surgical helmet assembly 200 and so that at least a portion of a lens 212 of the MR device 202 is exposed (at least partially optically) to the surgical environment through the inner frame 204 and the visor 208.

In operation, the surgeon 50 can wear the MR device 202 with the inner frame 204 attached thereto. Then, the visor 208 can be secured to the inner frame 204 to secure the hood 210 to the MR device 202 and to enclose the head of the surgeon 50 and to enclose or protect the MR device 202 and the inner frame 204 while exposing the lens 212 to the environment, optically, to allow the lens 212 and the MR device 202 to operate normally. Following a procedure or other use of the MR device 202, the visor 208 and the hood 210 can be separated from the inner frame 204, such as by disengaging the inner frame 204 from the visor 208, allowing the visor 208 and the hood 210 to be disposed and allowing the inner frame 204 and the MR device 202 to be reused in future procedures. Further details of the surgical helmet assembly 200 are discussed below.

Figure 2B:
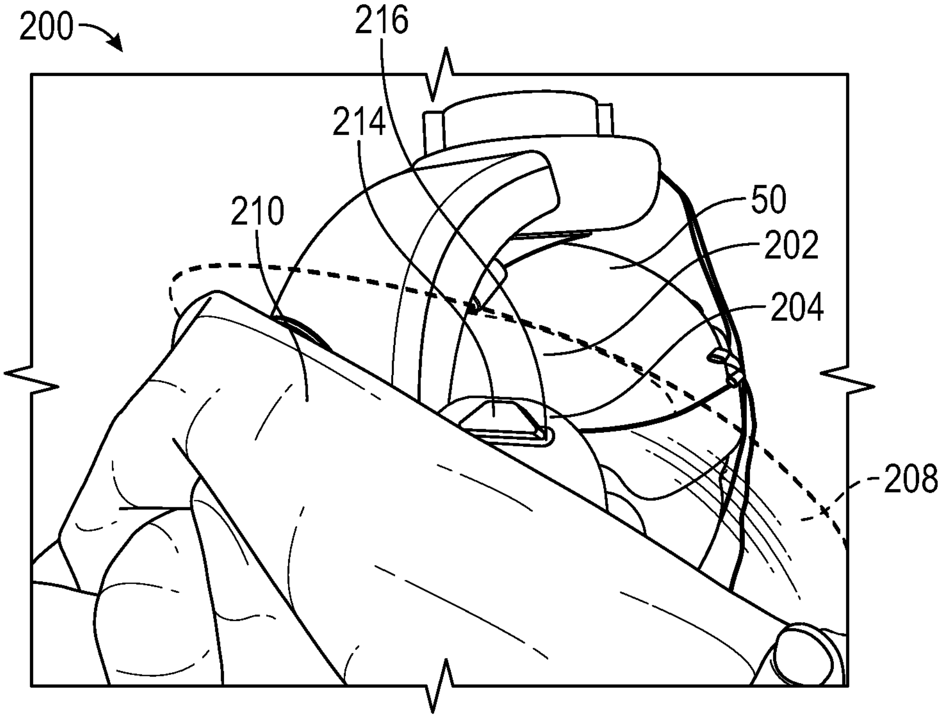
FIG. 2B illustrates a perspective view of a portion of a surgical helmet assembly.

FIG. 2B illustrates a perspective view of a portion of the surgical helmet assembly 200. The surgical helmet assembly 200 of FIG. 2B can be consistent with the surgical helmet assembly 200 of FIG. 2A. FIG. 2B shows that the inner frame 204 can include tabs 214 configured to be inserted into openings 216 of the visor 208 to secure the visor 208 to the inner frame 204. The tabs 214 can extend upward such as to help support a weight or mass of the visor 208 and the hood 210 when donned by the surgeon 50.

FIG. 2B also shows that the hood 210 can be connected to the visor 208 below the openings 216 to allow the hood 210 to cover the tabs 214 such that no component of the inner frame 204 or the MR device 202 is exposed to the environment. That is, every component of the inner frame 204 and the MR device 202 can be covered or protected by the hood 210 and the inner frame 204. Optionally, a battery of the MR device 202 can be exposed to the environment as discussed in further detail below.

Figure 3:
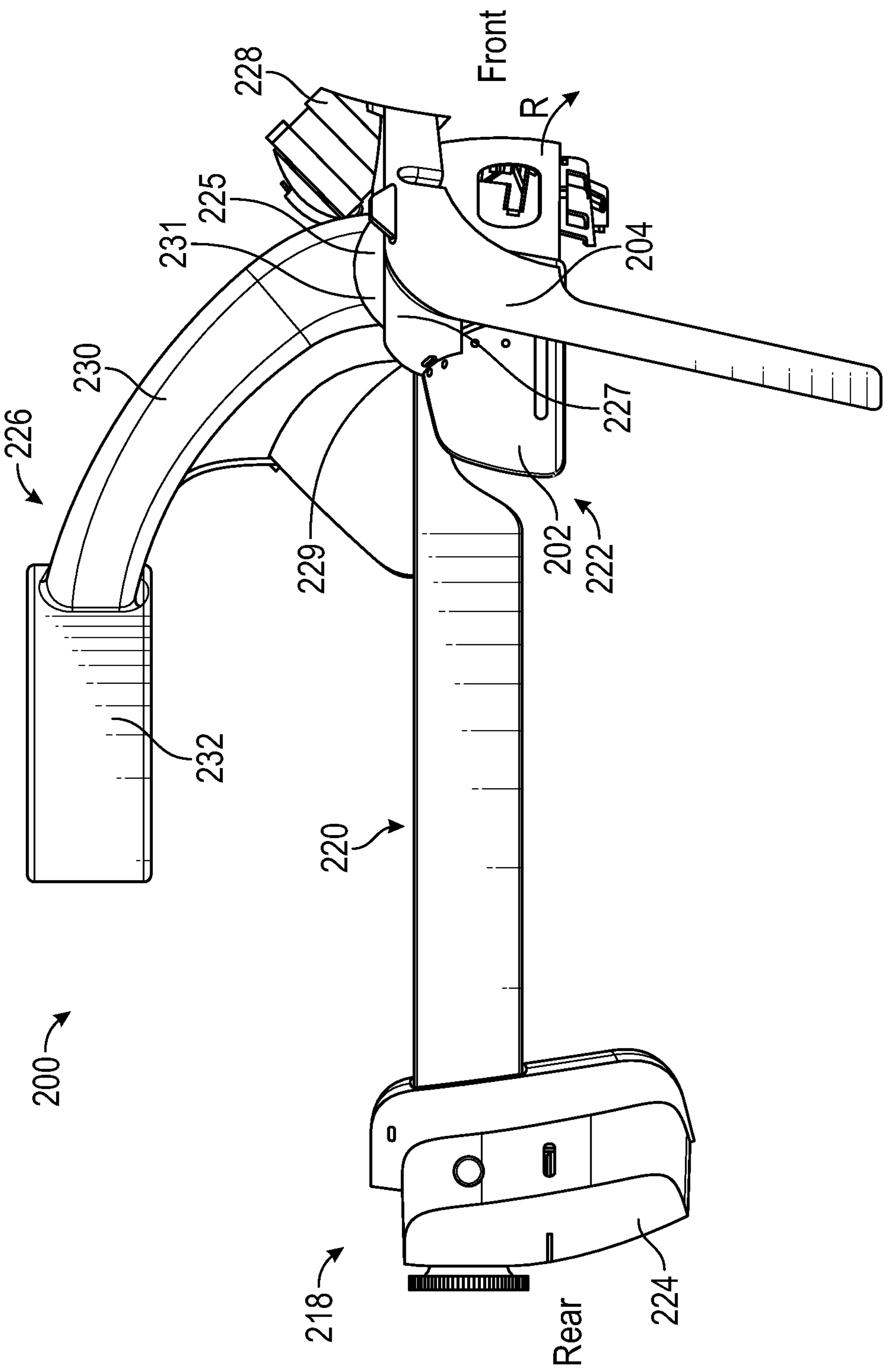
FIG. 3 illustrates a side view of a portion of a surgical helmet assembly.

FIG. 3 illustrates a side view of a portion of the surgical helmet assembly 200. FIG. 3 also shows orientation indicators Front and Rear. The surgical helmet assembly 200 can be consistent with the surgical helmet assembly 200 of FIGS. 1-2B discussed above; FIG. 3 shows additional details of the surgical helmet assembly 200.

For example, FIG. 3 shows that the MR device 202 can include a rear portion 218, a medial portion 220, and a front portion 222. The inner frame 204 can be connected to the front portion 222. The rear portion 218 can include a battery or power supply 224 configured to power the MR device 202. The medial portion 220 can be configured to connect the rear portion 218 to the front portion 222 and to support the MR device 202 on a head of the user (e.g., the surgeon 50).

In some examples, the front portion 222 can be movable with respect to the medial portion 220 and the rear portion 218, such as by rotating or pivoting. In such an example, the inner frame 204 can include a fixed portion 225 securable to the front portion 222 of the mixed reality device MR device 202. The inner frame 204 can also include a movable portion 227 rotatably coupled to the fixed portion 225. The movable portion 227 can be connected to the front portion 222 of the MR device 202, such that the movable portion 227 and the front portion 222 are rotatable with respect to the discharge fan 232 and the duct 230.

The MR device 202 can include a hinge 229 to enable rotation or movement of the front portion 222 with respect to the medial portion 220. The inner frame 204 can include a hinge or joint 231 connected to the fixed portion 225 and the movable portion 227 such that the fixed portion 225 and the movable portion 227 can be movable or rotatable with respect to each other, such as along the arc R of FIG. 3. Optionally, the joint 231 can be configured such that when the front portion 222 of the MR device 202 rotates about the hinge 229 with respect to the medial portion 220, the movable portion 227 rotates about the joint 231 with respect to the fixed portion 225 (and the duct 230 and the discharge fan 232) such that the rotation of the inner frame 204 can match the rotational direction and rate of rotation of the front portion 222 with respect to the medial portion 220. That is, the inner frame 204 can rotate in unison or together with the MR device 202 to allow the visor 208 and hood 210 to remain properly oriented during tilting of the MR device 202 for preferential viewing angle of the surgeon 50.

FIG. 3 also shows that the surgical helmet assembly 200 can include a cooling system 226 and a light 228, where the light 228 can be connected to a front portion of the inner frame 204. The light 228 can be any light emitting device configured to emit light toward a surgical field, such as through the visor 208 (not shown in FIG. 3). The light 228 can optionally be powered by the battery or power supply 224 or an internal battery (or other power source).

The cooling system 226 can include a duct 230 connected to the inner frame 204 and can include a fan 232 operable to generate an air stream to flow through the surgical helmet assembly 200. Further details of the cooling system 226 are discussed below.

Figure 4:
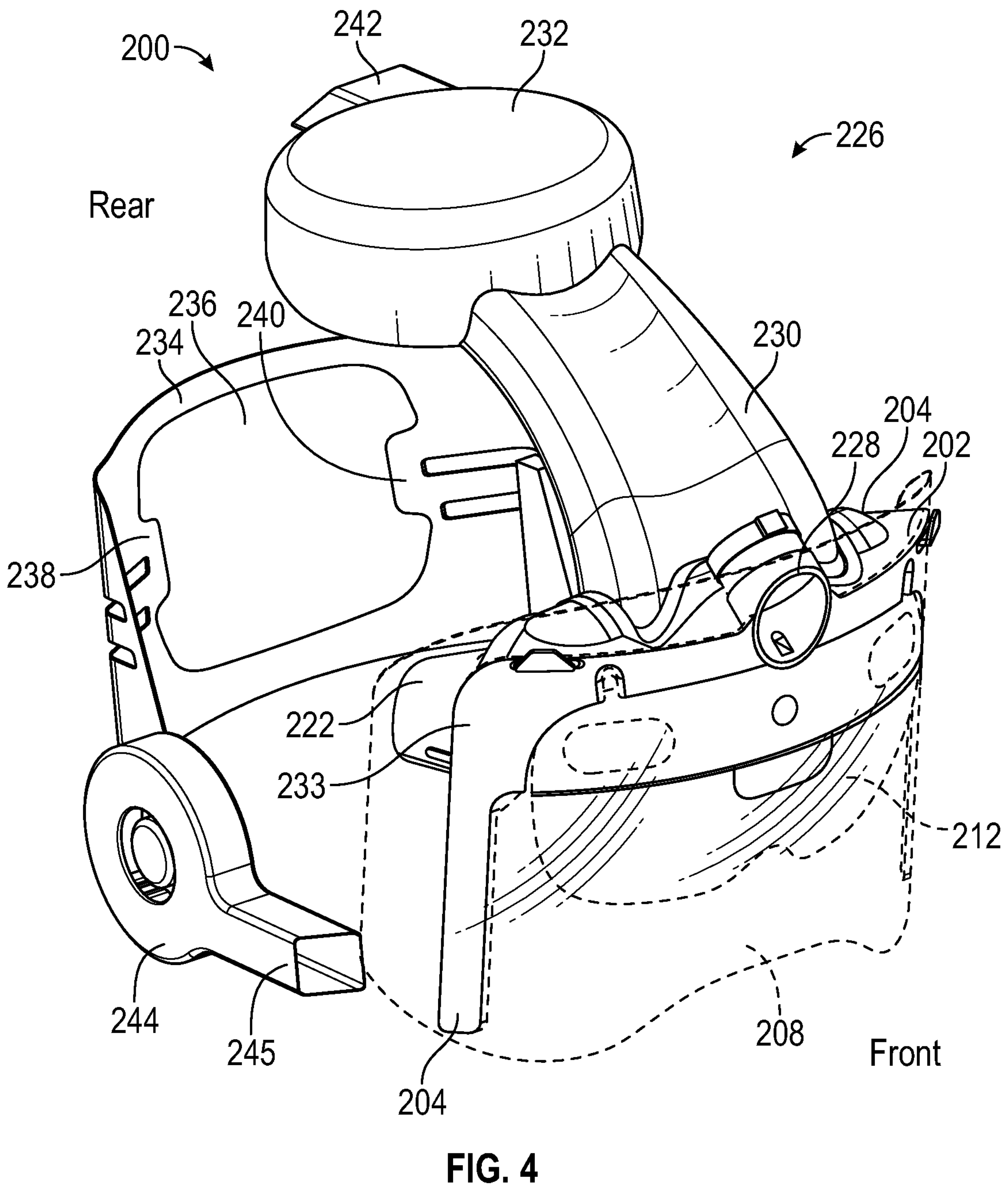
FIG. 4 illustrates an isometric view of a portion of a surgical helmet assembly.

FIG. 4 illustrates an isometric view of a portion of the surgical helmet assembly 200. FIG. 4 also shows orientation indicators Front and Rear. The surgical helmet assembly 200 can be consistent with the surgical helmet assembly 200 of FIGS. 1-2B discussed above; FIG. 4 shows additional details of the surgical helmet assembly 200.

For example, FIG. 4 shows that the inner frame 204 can include a front portion 233 connected to the front portion 222 of the MR device 202, which can include the lens 212. The inner frame 204 can also include a rear support 234, which can be connectable to the rear portion 218 of the MR device 202, such as to the battery or power supply 224 of the MR device 202. The rear support 234 can also be locatable near a posterior opening of the hood 210 (shown below) and configured to receive at least a portion of the battery or power supply 224 therein to connect the MR device 202 to the rear support 234. Optionally, the rear support 234 can include an opening 236 alignable with a posterior opening of the hood to position a rear portion of the MR device 202 at least partially outside of the surgical helmet assembly and outside of the hood 210.

The rear support 234 can also include a first projection 238 configured to extend inward into the support opening 236 and can include a second projection 240 configured to extend inward into the support opening 236 opposite the first projection 238. The first projection 238 and the second projection 240 can be insertable at least partially into opposite sides of the rear portion 218 of the mixed reality device MR device 202 to secure the surgical hood 210 or the rear support 234 to the rear portion of the mixed reality device MR device 202.

FIG. 4 also shows additional details of the cooling system 226. For example, FIG. 4 shows (more clearly) how the duct 230 can connect to the inner frame 204 rearward of the visor 208 at an inlet of the duct 230. The discharge fan 232 can include an inlet connected to the outlet of the duct 230 and the discharge fan 232 can include an outlet connected to a discharge duct 242. The discharge duct 242 can extend at least partially through the surgical hood 210 and can be configured to discharge the air stream out of the surgical hood 210. Optionally, the discharge duct 242 can engage with a filter or other portion of the hood 210 to limit exposure of the discharge duct 242 while allowing the air stream to exhaust through the hood 210. The discharge fan 232 can be operable to produce the air stream to flow into the surgical hood 210, through the inner frame 204, through the duct 230, through the discharge duct 242, and out the surgical hood 210.

The cooling system 226 can also include an inlet fan 244 connected to the inner frame 204 such as to the rear support 234. The inlet fan 244 can include an inlet duct 245 that can extend at least partially through the hood 210 or can be connected to an opening in the hood 210. Optionally, the inlet duct 245 can engage with a filter or other portion of the hood 210 to limit exposure of the inlet duct 245 while allowing the air stream to be taken in through the hood 210.

The inlet fan 244 can be operable to draw the air stream from outside of the surgical hood 210 into the surgical hood 210 such that fresh air may enter the inner frame 204 to cool (e.g., convectively or conductively) components of the MR device 202 or the user wearing the surgical helmet assembly 200 during a procedure.

FIG. 4 also shows, more clearly, that the light 228 can be connected to the inner frame 204 and can be configured to direct light through the visor 208 and toward a surgical field. Optionally, the light 228 can be connected to the movable portion 227 of the inner frame 204 such that the light 228 can move with the movable portion 227 and the front portion 222 to illuminate a portion of the surgical field where the surgeon 50 is viewing.

Figure 5:
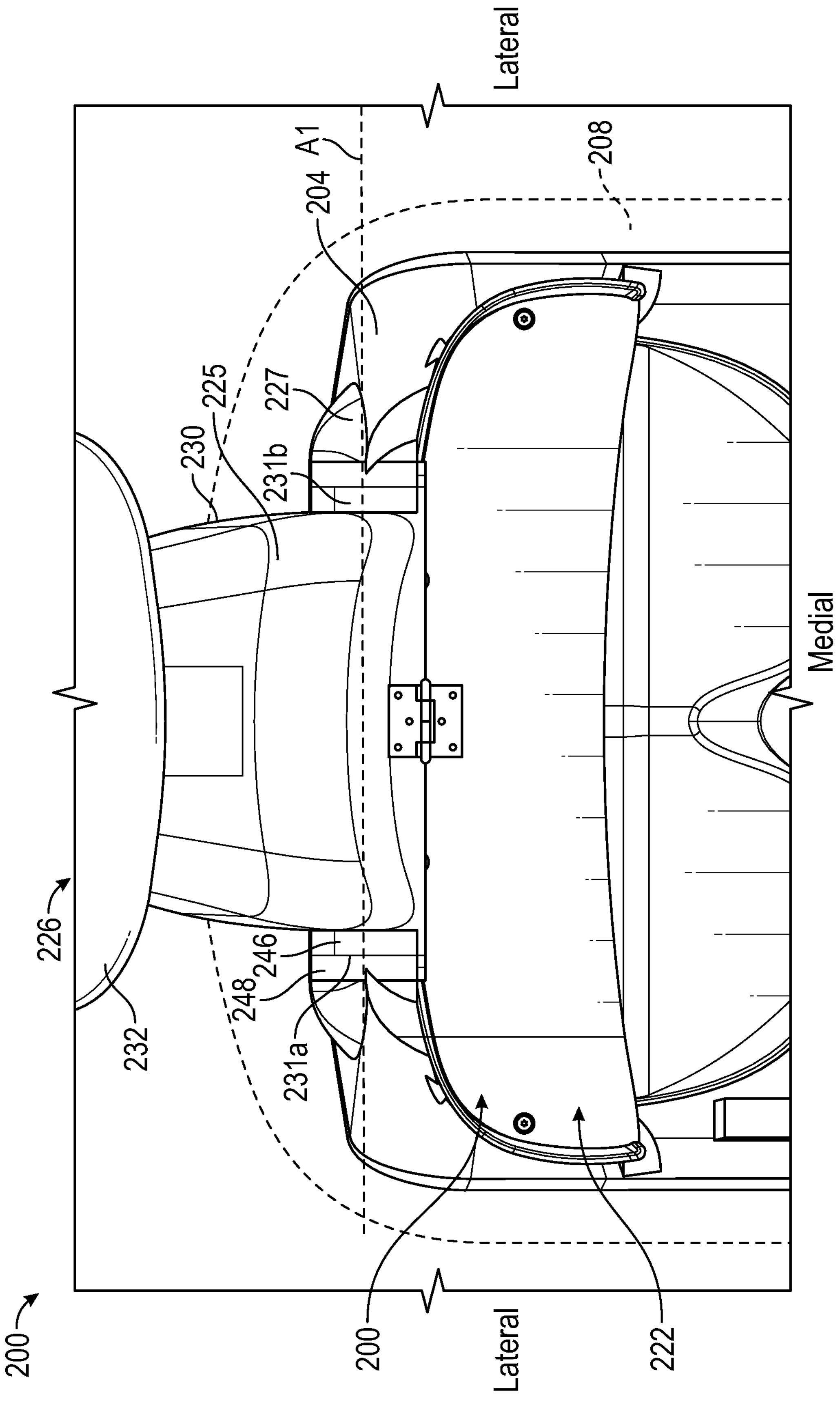
FIG. 5 illustrates an isometric view of a portion of a surgical helmet assembly.

FIG. 5 illustrates an isometric view of a portion of the surgical helmet assembly 200. FIG. 5 also shows orientation indicators Lateral and Medial. The surgical helmet assembly 200 can be consistent with the surgical helmet assembly 200 of FIGS. 1-4 discussed above; FIG. 5 shows additional details of the surgical helmet assembly 200.

For example, FIG. 5 shows how the fixed portion 225 and the movable portion 227 of the inner frame 204 can connect at the joint 231. The inner frame 204 can include one of joints **231*a* and 231*b* on each side of the duct 230. Each joint 231 can include an inner ring 246 and an outer ring 248. The inner ring 246 can be connected to the fixed portion 225 (and the duct 230) and the outer ring 248 can be connected to the movable portion 227. The inner ring 246 and the outer ring 248 can be rotatably connected to form the joint such that the inner ring 246 and the outer ring 248 rotate with respect to each other to allow the movable portion 227 to rotate or move with respect to the fixed portion 225**.

FIG. 5 also shows that the front portion 222 (e.g., the movable portion 227) can be connected to the inner frame 204 such that the movable portion 227, the front portion 222 of the MR device 202, and the visor 208 can move or rotate about an axis Al with respect to the fixed portion 225, the duct 230, and the discharge fan 232.

Figure 6A:
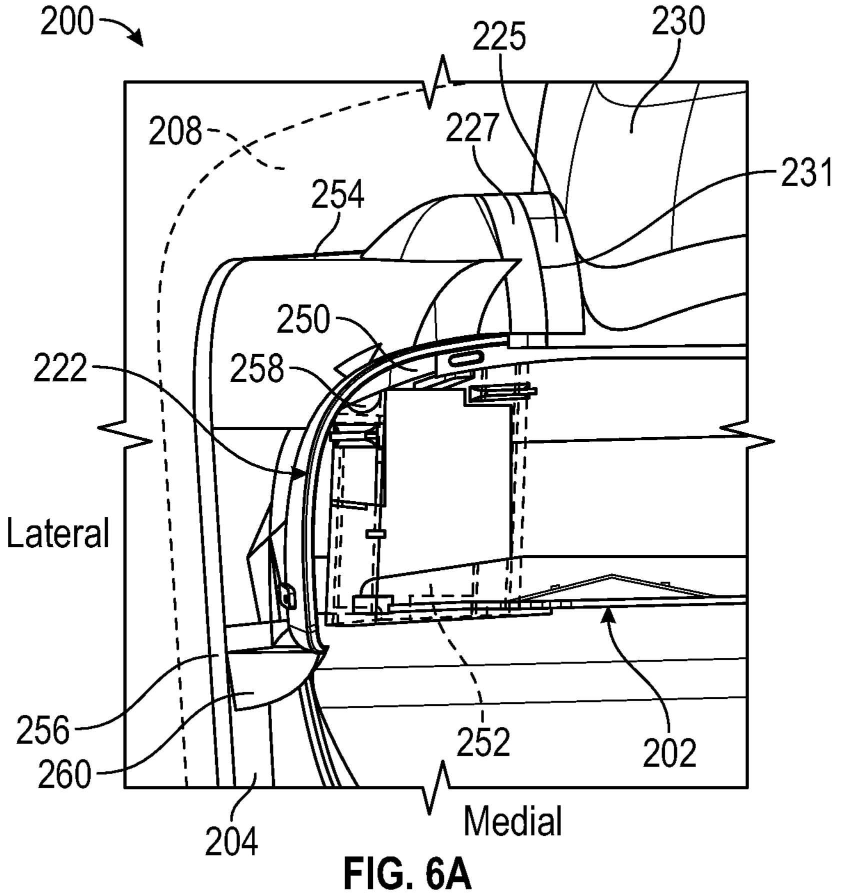
FIG. 6A illustrates an isometric view of a portion of a surgical helmet assembly.
Figure 6B:
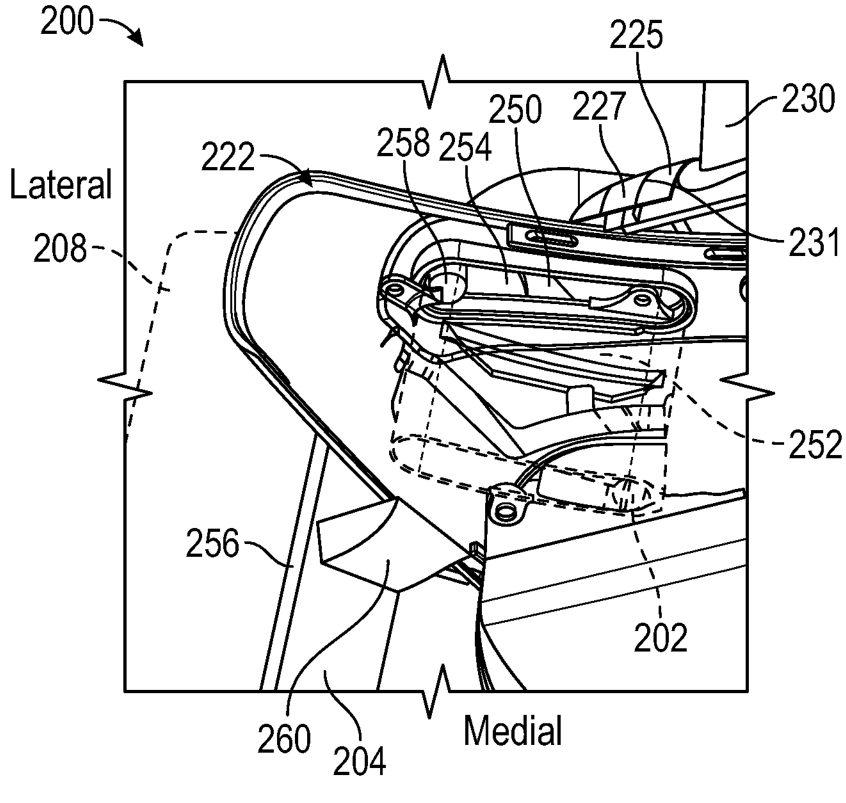
FIG. 6B illustrates an isometric view of a portion of a surgical helmet assembly.

FIG. 6A illustrates an isometric view of a portion of the surgical helmet assembly 200. FIG. 6B illustrates an isometric view of a portion of the surgical helmet assembly 200. FIGS. 6A and 6B are discussed together below. FIGS. 6A and 6B also show orientation indicators Lateral and Medial. The surgical helmet assembly 200 can be consistent with the surgical helmet assembly 200 of FIGS. 1-5 discussed above; FIGS. 6A and 6B show additional details of the surgical helmet assembly 200.

For example, FIGS. 6A and 6B show how the inner frame 204 can be secured to the MR device 202. More specifically, FIGS. 6A and 6B show that the MR device 202 can include an opening 250 in the front portion 222, such as along a top portion or plate or component of the MR device 202. The MR device 202 can also include a pillar or support 252 connected to the top portion and aligned with the opening 250. The support 252 can define a bore or opening extending at least partially therethrough and aligned with the opening 250.

FIGS. 6A and 6B also show that the inner frame 204 can include an upper portion 254 and a lower portion 256. The upper portion 254 can include a projection 258 extending downward therefrom and insertable into the slot 250 of the MR device 202. The lower portion 256 can include a tab 260 (or shelf) extending laterally inward and engageable with a bottom portion or frame of the front portion 222 of the MR device 202. When the projection 258 is inserted into the opening 250 (and optionally the support 252) and when the tab 260 is engaged with the front portion 222, the inner frame 204 can be secured to the MR device 202. The inner frame 204 can include a projection 258 and shelf 260 on each lateral side of the inner frame 204 such that the inner frame 204 can include a pair of projections and a pair of shelves. In this way, the inner frame 204 can be releasably securable to the MR device 202 without the use of fasteners (e.g., screws or hook and loop fasteners).

Figure 7:
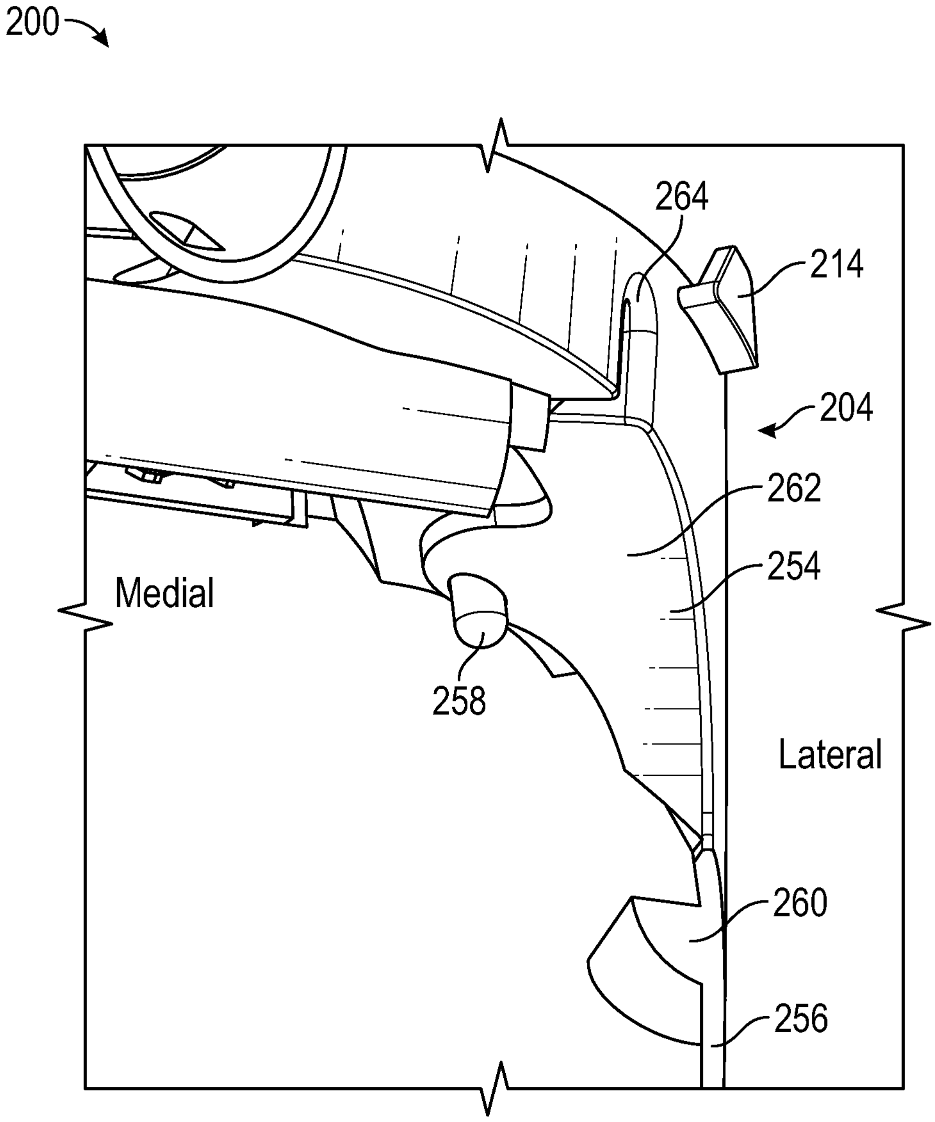
FIG. 7 illustrates an isometric view of a portion of a surgical helmet assembly.

FIG. 7 illustrates an isometric view of the inner frame 204 of the surgical helmet assembly 200. FIG. 7 also shows orientation indicators Lateral and Medial. The surgical helmet assembly 200 can be consistent with the surgical helmet assembly 200 of FIGS. 1-6B discussed above; FIG. 7 shows additional details of the surgical helmet assembly 200. For example, FIG. 7 shows how the projection 258 can extend downward from the upper portion 254 of the inner frame 204. The projection 258 can be a boss, projection, protuberance, or the like, and can be sized and shaped to be inserted into the MR device 202, as discussed above. The projection 258 can optionally be rounded at a distal tip thereof, such as to help reduce friction between the projection 258 and the MR device 202 and to help guide insertion of the projection 258 into the opening 250 of the MR device 202.

FIG. 7 also shows that the tab 260 can have a shape of a quarter cylinder with a flat surface facing upward or opposing the projection 258. The tab 260 can have other shapes in other examples, such as a rectangular prism, or the like. The tab 260 and the projection 258 can operate as a clamp on the MR device 202 by engaging a top and bottom portion of the MR device 202 where the projection 258 can limit backing out or separation of the inner frame 204 from the MR device 202.

FIG. 7 also shows that the upper portion 254 of the inner frame 204 can include a curved surface 262 which can be engageable with the MR device 202. The curved surface 262 can be shaped to be complimentary to at least a portion of an outer surface of the MR device 202 such as to improve mating between the inner frame 204 and the MR device 202 when the inner frame 204 is connected to the MR device 202.

FIG. 7 also illustrates that the inner frame 204 (such as the lower portion 256) can be relatively thin, which can allow the lower portion 256 to flex with respect to the upper portion 254, such as to flex laterally outward. In this way, the projection 258 can be inserted into the opening 250 (as shown above) and then the lower portion 256 can be flexed or bent laterally outward allowing the tab 260 to clear a laterally outer portion or surface of the MR device 202 such that the tab 260 can be inserted or positioned below the MR device 202 or hooked around the MR device 202. Such flexibility can also allow the inner frame 204 to be disengaged from the MR device 202, allowing the inner frame 204 to connected and disconnected from the MR device 202 without fasteners such as screws or hook and loop fasteners.

FIG. 7 also shows that the inner frame 204 can include a recess 264, which can be a bore, opening, passage, or the like configured to expose one or more microphones or sensors of the MR device 202 to the surgical environment. FIG. 7 also more clearly shows how the tabs 214 can extend upward from an outer front surface of the inner frame 204, such as to insert into the openings 216 of the visor 208.

Figure 8A:
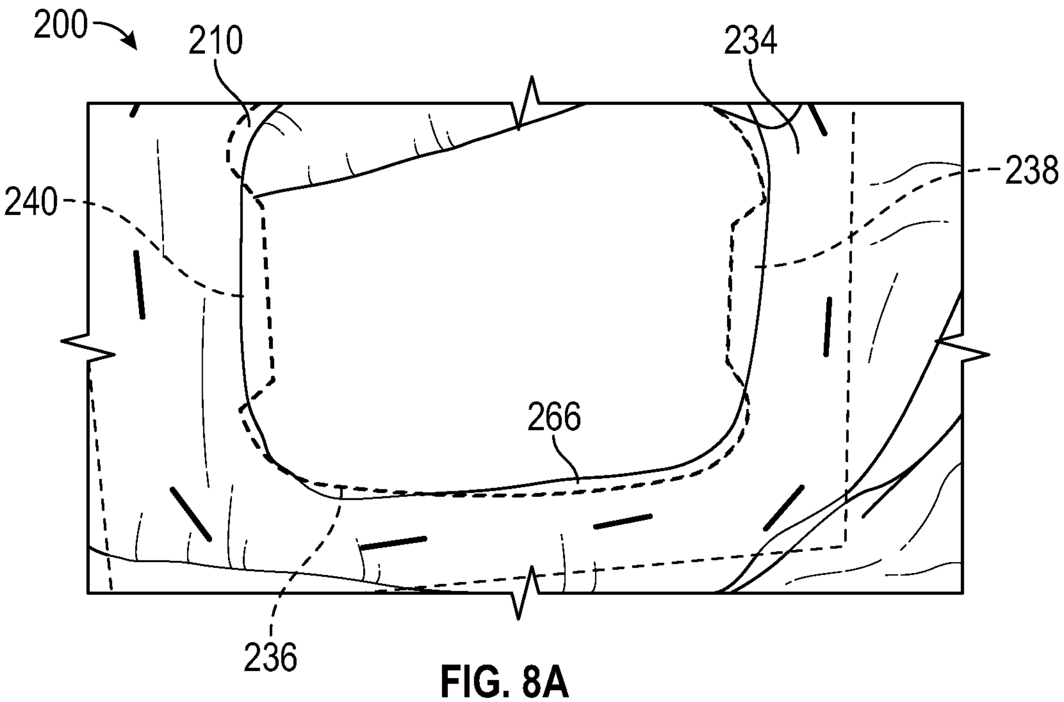
FIG. 8A illustrates a perspective view of a portion of a surgical helmet assembly.
Figure 8B:
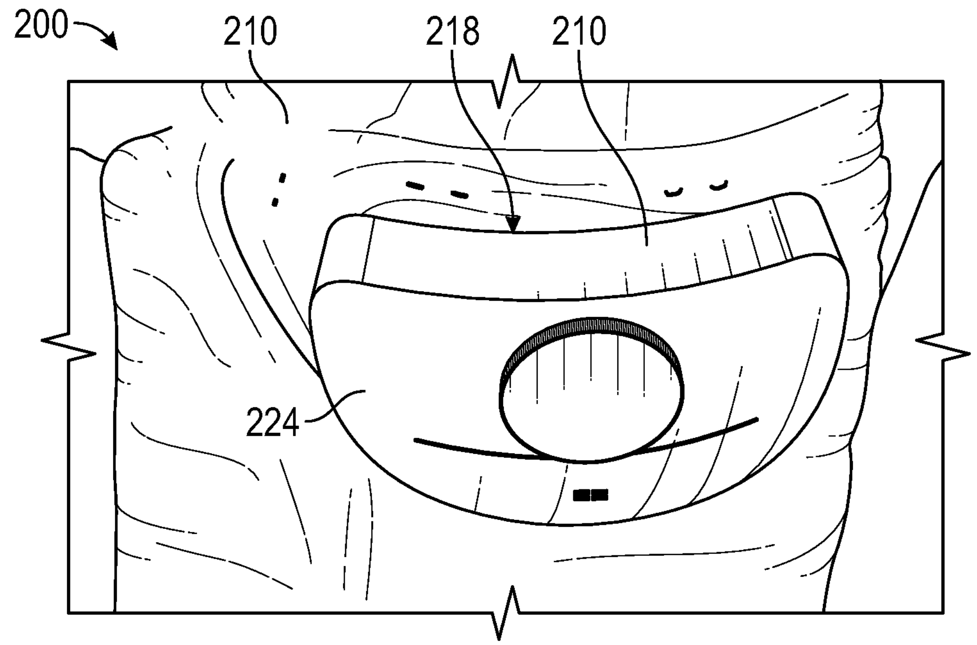
FIG. 8B illustrates a perspective view of a portion of a surgical helmet assembly.

FIG. 8A illustrates a perspective view of a portion of the surgical helmet assembly 200. FIG. 8B illustrates a perspective view of a portion of the surgical helmet assembly 200. FIGS. 8A and 8B are discussed together below. The surgical helmet assembly 200 can be consistent with the surgical helmet assembly 200 of FIGS. 1-7 discussed above; FIGS. 8A and 8B show additional details of the surgical helmet assembly 200.

For example, FIG. 8A shows how the rear support 234 can include the support opening 236 that can align with an opening 266 of the hood 210 such that the first projection 238 and the second projection 240 can extend into the support opening 236 and the opening 266. FIG. 8B shows that the battery or power supply 224 of the rear portion 218 can be located outside the hood 210 when the first projection 238 and the second projection 240 are engaged with the rear portion 218 to secure the rear portion 218 and the battery or power supply 224 to the rear support 234. In this way, heat generated by the battery or power supply 224 can be rejected to the environment instead of transferred to an environment within the hood 210, helping to maintain a comfortable work environment within the hood 210 for the surgeon 50.

NOTES AND EXAMPLES

The following, non-limiting examples, detail certain aspects of the present subject matter to solve the challenges and provide the benefits discussed herein, among others.

Example 1 is a surgical helmet assembly securable to a mixed reality device, the assembly comprising: an inner frame securable to the mixed reality device; an outer frame releasably securable to the inner frame, the outer frame including a visor to optically expose the mixed reality device to a surgical field; and a surgical hood connected to the outer frame and configured to cover at least a portion of a head of a user, the surgical hood defining a posterior opening to receive a rear portion of the mixed reality device at least partially therethrough to position the rear portion at least partially outside of the surgical helmet assembly.

In Example 2, the subject matter of Example 1 optionally includes the inner frame including: a rear support locatable near the posterior opening, the rear support releasably securable to the mixed reality device, and the rear support defining a support opening alignable with the posterior opening to position the rear portion of the mixed reality device at least partially outside of the surgical helmet assembly.

In Example 3, the subject matter of Example 2 optionally includes the rear support including: a first projection configured to extend inward into the support opening; and a second projection configured to extend inward into the support opening opposite the first projection, the first projection and the second projection insertable at least partially into opposite sides of the rear portion of the mixed reality device to secure the surgical hood to the rear portion of the mixed reality device.

In Example 4, the subject matter of Example 3 optionally includes wherein the rear support is configured to position a battery pack of the rear portion of the mixed reality device at least partially outside of the surgical helmet assembly.

In Example 5, the subject matter of any one or more of Examples 1-4 optionally include a cooling system connected to the inner frame and locatable at least partially within the surgical hood, the cooling system operable to deliver an air stream to the inner frame, the mixed reality device, and the surgical hood.

In Example 6, the subject matter of Example 5 optionally includes the cooling system comprising: a duct including an inlet connected to the inner frame and including an outlet; a discharge fan including an outlet and including an inlet connected to the outlet of the duct, the discharge fan operable to produce the air stream to flow into the surgical hood, through the inner frame, through the duct, and out the surgical hood.

In Example 7, the subject matter of Example 6 optionally includes the cooling system comprising: a discharge duct connected to the outlet of the discharge fan, the discharge duct extending through the surgical hood and configured to discharge the air stream out of the surgical hood.

In Example 8, the subject matter of any one or more of Examples 6-7 optionally include the cooling system comprising: an inlet fan connected to the inner frame and operable to draw the air stream from outside of the surgical hood into the surgical hood.

In Example 9, the subject matter of Example 8 optionally includes the inner frame comprising: a front portion connected to a lens of the mixed reality device; and a rear support locatable near the posterior opening, the rear support releasably securable to the mixed reality device, the inlet fan connected to the rear support.

In Example 10, the subject matter of any one or more of Examples 6-9 optionally include wherein the inner frame includes a movable portion securable to the mixed reality device and includes a fixed portion rotatably coupled to the movable portion, the fixed portion connected to the duct, such that a portion of the mixed reality device and a portion of the inner frame are rotatable with respect to the duct and the discharge fan.

In Example 11, the subject matter of any one or more of Examples 1-10 optionally include wherein the inner frame includes an upper portion and a lower portion, the upper portion including a projection extending downward therefrom and insertable into a slot of the mixed reality device, the lower portion including a tab extending laterally inward and engageable with the mixed reality device to, together with the projection, secure the inner frame to the mixed reality device.

In Example 12, the subject matter of any one or more of Examples 1-11 optionally include wherein the inner frame includes an upper portion and a lower portion, the upper portion including a pair of projections extending downward from opposite sides of the upper portion, each projection insertable into a slot of a pair of slots of the mixed reality device, the lower portion including a pair of tabs extending laterally inward from opposite sides of the lower portion, each tab of the pair of tabs engageable with the mixed reality device to, together with the pair of projections, secure the inner frame to the mixed reality device.

In Example 13, the subject matter of any one or more of Examples 1-12 optionally include wherein the inner frame includes a movable portion securable to the mixed reality device and includes a fixed portion rotatably coupled to the movable portion.

In Example 14, the subject matter of any one or more of Examples 1-13 optionally include a light assembly connected to the inner frame and configured to emit light through the visor of the outer frame and toward a surgical field.

In Example 15, the subject matter of any one or more of Examples 1-14 optionally include the inner frame comprising: a recess configured to expose a microphone of the mixed reality device.

Example 16 is a surgical helmet assembly securable to a mixed reality device, the assembly comprising: an inner frame securable to the mixed reality device; a visor releasably securable to the inner frame, the visor to optically expose the mixed reality device to a surgical field; and a surgical hood connected to the visor and configured to cover at least a portion of a head of a user.

In Example 17, the subject matter of Example 16 optionally includes wherein the inner frame includes an upper portion and a lower portion, the upper portion including a projection extending downward therefrom and insertable into a slot of the mixed reality device, the lower portion including a tab extending laterally inward and engageable with the mixed reality device to, together with the projection, secure the inner frame to the mixed reality device.

In Example 18, the subject matter of any one or more of Examples 16-17 optionally include wherein the inner frame includes a fixed portion securable to the mixed reality device and includes a movable portion rotatably coupled to the fixed portion.

In Example 19, the subject matter of any one or more of Examples 16-18 optionally include wherein the surgical hood defines a posterior opening to receive a rear portion of the mixed reality device at least partially therethrough to position the rear portion at least partially outside of the surgical helmet assembly.

In Example 20, the subject matter of Example 19 optionally includes the inner frame including: a rear support locatable near the posterior opening, the rear support releasably securable to the mixed reality device, and the rear support defining a support opening alignable with the posterior opening to position the rear portion of the mixed reality device at least partially outside of the surgical helmet assembly.

In Example 21, the apparatuses, systems, or methods of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A surgical helmet assembly securable to a mixed reality device, the assembly comprising:

an inner frame securable to the mixed reality device;

an outer frame releasably securable to the inner frame, the outer frame including a visor to optically expose the mixed reality device to a surgical field; and a surgical hood connected to the outer frame and configured to cover at least a portion of a head of a user, the surgical hood defining a posterior opening to receive a rear portion of the mixed reality device at least partially therethrough to position the rear portion at least partially outside of the surgical helmet assembly.

2. The surgical helmet assembly of claim 1, the inner frame including:

a rear support locatable near the posterior opening, the rear support releasably securable to the mixed reality device, and the rear support defining a support opening alignable with the posterior opening to position the rear portion of the mixed reality device at least partially outside of the surgical helmet assembly.

3. The surgical helmet assembly of claim 2, the rear support including:

a first projection configured to extend inward into the support opening; and a second projection configured to extend inward into the support opening opposite the first projection, the first projection and the second projection insertable at least partially into opposite sides of the rear portion of the mixed reality device to secure the surgical hood to the rear portion of the mixed reality device.

4. The surgical helmet assembly of claim 3, wherein the rear support is configured to position a battery pack of the rear portion of the mixed reality device at least partially outside of the surgical helmet assembly.

5. The surgical helmet assembly of claim 1, comprising: a cooling system connected to the inner frame and locatable at least partially within the surgical hood, the cooling system operable to deliver an air stream to the inner frame, the mixed reality device, and the surgical hood.

6. The surgical helmet assembly of claim 5, the cooling system comprising:

a duct including an inlet connected to the inner frame and including an outlet;

a discharge fan including an outlet and including an inlet connected to the outlet of the duct, the discharge fan operable to produce the air stream to flow into the surgical hood, through the inner frame, through the duct, and out the surgical hood.

7. The surgical helmet assembly of claim 6, the cooling system comprising:

a discharge duct connected to the outlet of the discharge fan, the discharge duct extending through the surgical hood and configured to discharge the air stream out of the surgical hood.

8. The surgical helmet assembly of claim 6, the cooling system comprising:

an inlet fan connected to the inner frame and operable to draw the air stream from outside of the surgical hood into the surgical hood.

9. The surgical helmet assembly of claim 8, the inner frame comprising:

a front portion connected to a lens of the mixed reality device; and a rear support locatable near the posterior opening, the rear support releasably securable to the mixed reality device, the inlet fan connected to the rear support.

10. The surgical helmet assembly of claim 6, wherein the inner frame includes a movable portion securable to the mixed reality device and includes a fixed portion rotatably coupled to the movable portion, the fixed portion connected to the duct, such that a portion of the mixed reality device and a portion of the inner frame are rotatable with respect to the duct and the discharge fan.

11. The surgical helmet assembly of claim 1, wherein the inner frame includes an upper portion and a lower portion, the upper portion including a projection extending downward therefrom and insertable into a slot of the mixed reality device, the lower portion including a tab extending laterally inward and engageable with the mixed reality device to, together with the projection, secure the inner frame to the mixed reality device.

12. The surgical helmet assembly of claim 1, wherein the inner frame includes an upper portion and a lower portion, the upper portion including a pair of projections extending downward from opposite sides of the upper portion, each projection insertable into a slot of a pair of slots of the mixed reality device, the lower portion including a pair of tabs extending laterally inward from opposite sides of the lower portion, each tab of the pair of tabs engageable with the mixed reality device to, together with the pair of projections, secure the inner frame to the mixed reality device.

13. The surgical helmet assembly of claim 1, wherein the inner frame includes a movable portion securable to the mixed reality device and includes a fixed portion rotatably coupled to the movable portion.

14. The surgical helmet assembly of claim 1, comprising:

a light assembly connected to the inner frame and configured to emit light through the visor of the outer frame and toward a surgical field.

15. The surgical helmet assembly of claim 1, the inner frame comprising:

a recess configured to expose a microphone of the mixed reality device.

16. A surgical helmet assembly securable to a mixed reality device, the assembly comprising:

an inner frame including a fixed portion securable to the mixed reality device, and the inner frame including a movable portion rotatably coupled to the fixed portion;

a visor releasably securable to the inner frame, the visor to optically expose the mixed reality device to a surgical field; and a surgical hood connected to the visor and configured to cover at least a portion of a head of a user.

17. The surgical helmet assembly of claim 16, wherein the inner frame includes an upper portion and a lower portion, the upper portion including a projection extending downward therefrom and insertable into a slot of the mixed reality device, the lower portion including a tab extending laterally inward and engageable with the mixed reality device to, together with the projection, secure the inner frame to the mixed reality device.

18. The surgical helmet assembly of claim 16, wherein the surgical hood defines a posterior opening to receive a rear portion of the mixed reality device at least partially therethrough to position the rear portion at least partially outside of the surgical helmet assembly.

19. The surgical helmet assembly of claim 18, the inner frame including:

a rear support locatable near the posterior opening, the rear support releasably securable to the mixed reality device, and the rear support defining a support opening alignable with the posterior opening to position the rear portion of the mixed reality device at least partially outside of the surgical helmet assembly.

* * * * *